US009895551B2

United States Patent
Fillmore et al.

(10) Patent No.: US 9,895,551 B2
(45) Date of Patent: Feb. 20, 2018

(54) BRACHYTHERAPY APPLICATOR DEVICE AND METHOD OF USE THEREOF

(71) Applicant: KOBOLD, LLC, Liberty Lake, WA (US)

(72) Inventors: Spencer J. Fillmore, Greenacres, WA (US); Christopher M. Lee, Greenacres, WA (US)

(73) Assignee: KOBOLD, LLC, Liberty Lake, WA (US)

( * ) Notice: Subject to any disclaimer, the term of this patent is extended or adjusted under 35 U.S.C. 154(b) by 0 days.

(21) Appl. No.: 14/872,591

(22) Filed: Oct. 1, 2015

(65) Prior Publication Data
US 2016/0096039 A1 Apr. 7, 2016

Related U.S. Application Data

(63) Continuation of application No. 14/334,501, filed on Jul. 17, 2014, now Pat. No. 9,180,311, which is a (Continued)

(51) Int. Cl.
*A61N 5/10* (2006.01)

(52) U.S. Cl.
CPC .......... *A61N 5/1007* (2013.01); *A61N 5/1014* (2013.01); *A61N 5/1016* (2013.01); *A61N 2005/1009* (2013.01)

(58) Field of Classification Search
CPC ...... A61N 5/10; A61N 5/1001; A61N 5/1002; A61N 5/1007; A61N 5/1014; A61N 5/1015; A61N 5/1016
See application file for complete search history.

(56) References Cited

U.S. PATENT DOCUMENTS 4,292,960 A 10/1981 Paglione
4,331,131 A 5/1982 Kumar
(Continued)

FOREIGN PATENT DOCUMENTS

FR 2401669 A1 3/1979
WO 2007149578 A2 12/2007
(Continued)

OTHER PUBLICATIONS

"Intracavitary HDR Brachytherapy CT Compatible FSD T&O Applicator," Mick Radio-Nuclear Instruments, Inc., The Brachytherapy Company; www.micknuclear.com; 2003.
(Continued)

*Primary Examiner* — Charles A Marmor, II
*Assistant Examiner* — Carrie R Dorna
(74) *Attorney, Agent, or Firm* — Sterling D. Fillmore; Workman Nydegger

(57) ABSTRACT

An applicator device is provided including a connecting unit. The connecting unit includes a first connector coupled to a first colpostat and a second connector coupled to a second colpostat. The first connector includes a first contact portion and a body portion, the first contact portion being immovably fixed to the body portion. The second connector includes a second contact portion and a third contact portion, the second contact portion being configured to contact and pivotally engage the first contact portion. The first connector further includes a fourth contact portion configured to contact the third contact portion. The second contact portion and the third contact portion are disposed between the first contact portion and the fourth contact portion, and the first contact portion are disposed in closer proximity to a point of delivery of a radiation source than the second, third, or fourth contact portions.

23 Claims, 30 Drawing Sheets

Related U.S. Application Data continuation of application No. PCT/US2013/057413, filed on Aug. 29, 2013.

(56) References Cited

U.S. PATENT DOCUMENTS

| | | | |
|---|---|---|---|
| 5,012,357 | A | 4/1991 | Schoeppel et al. |
| 5,562,594 | A | 10/1996 | Weeks |
| 6,699,171 | B2 | 3/2004 | Harmon |
| 7,666,130 | B2 | 2/2010 | Mick |
| 8,033,979 | B2 | 10/2011 | Mick |
| 2002/0032449 | A1 | 3/2002 | Rota et al. |
| 2003/0153803 | A1 | 8/2003 | Harmon |
| 2008/0064916 | A1 | 3/2008 | Mick |
| 2010/0152520 | A1 | 6/2010 | Mick |
| 2012/0123188 | A1 | 5/2012 | Rahimian |
| 2012/0277518 | A1 | 11/2012 | Mick et al. |
| 2013/0006097 | A1 | 1/2013 | Mick et al. |
| 2014/0121444 | A1 | 5/2014 | Van Erp et al. |
| 2015/0065784 | A1 | 3/2015 | Fillmore et al. |

FOREIGN PATENT DOCUMENTS

| | | | |
|---|---|---|---|
| WO | 2011011731 | A2 | 1/2011 |
| WO | 2012149417 | A1 | 11/2012 |
| WO | 2013177249 | A1 | 11/2013 |
| WO | 2014036337 | A2 | 3/2014 |
| WO | 2016073596 | A1 | 5/2016 |

OTHER PUBLICATIONS

"Varian BrachyTherapy Applicators and Accessories;" Varian Medical Systems, Inc.,www.varian.com/brachytherapy; 2011.

"HDR CT Compatible Henshke Type Gyn Applicator Gamma-med/Vari-Source with Click Fit Connector (w/Unshielded Ovoids)," Mick Radio-Nuclear Instruments, Inc., Catalog #0508, Apr. 13, 2009.

"Intracavitary HDR Brachytherapy CT Compatible Henschke T&O Applicator," Mick Radio-Nuclear Instruments, Inc., The Brachytherapy Company; www.micknuclear.com; 2003.

"HDR CT Compatible Henshke Type Gyn Applicator Gamma-med/Vari-Source with Click Fit Connector (w/Unshielded Ovoids)," Mick Radio-Nuclear Instruments, Inc., Catalog #0508,May 18, 2011.

"Modified Henschke Type Cervix Applicator Kit" Mick Radio-Nuclear Instruments, Inc., Catalog #6402-93M ,May 27, 2010.

"HDR CT Compatible Fletcher-Suit-Delclos (FSD) Applicator (with Unshielded Ovoids & without interface Connectors) for Nucletron HDR," Catalog #0819, Instruction Manual, Mick Radio-Nuclear Instruments, Inc., Dec. 16, 2009.

"HDR CT Compatible Fletcher-Suit-Delclos (FSD) Applicator (with Unshielded Ovoids) for GammaMed/Vari-Source HDR," Catalog #0612, Instruction Manual, Mick Radio-Nuclear Instruments, Inc., Mar. 11, 2010.

"HDR CT Compatible Fletcher-Suit-Delclos (FSD) Applicator (with Unshielded Ovoids) for MulitSource HDR" Catalog #0817, Instruction Manual, Mick Radio-Nuclear Instruments, Inc., Dec. 16, 2009.

International Search Report and Written Opinion of corresponding of PCT Application No. PCT/US2013/057413 received on Feb. 7, 2014.

European Search Report from corresponding European Application No. 13832673.1, Jul. 5, 2016.

Varian: Varian Brachytherapy Applicators and Accessories, Varian medical systems, Inc, Jan. 2011, XP055339041,148 Pages.

International Search Report from PCT Application No. PCT/US20161057359, dated Feb. 3, 2017.

BRACHYTHERAPY APPLICATOR DEVICE AND METHOD OF USE THEREOF

This application is a continuation of U.S. patent application Ser. No. 14/334,501 filed Jul. 17, 2014, which is a continuation of Application No. PCT/US2013/057413 filed Aug. 29, 2013, the entirety of which are incorporated herein by reference

BACKGROUND

Technical Field

The present disclosure relates generally to an applicator device for use in delivering radiation therapy, and more particularly to a brachytherapy applicator device for use in supplying a radiation source to an internal tumor.

Description of the Related Art

Brachytherapy is a form of cancer treatment in which radiation sources are placed inside a patient's body to irradiate an internal tumor. Thus, in brachytherapy, a radioactive source may be placed in or around a tumor. Brachytherapy thus has the advantage of delivering high doses of ionizing radiation to small volumes of tissue, combined with a rapid fall off of dose such that distant tissue may be spared. It thus has provided excellent results for localized control of various cancers, including, for example, cancer of the vagina, cervix, or uterus.

Afterloading is a commonly used radiation delivery technique wherein a non-radioactive applicator may be first positioned in the treatment site and then the applicator may be loaded with a radiation source. Once the applicator is correctly positioned in the patient the applicator may be connected to an afterloader machine, which contains the radioactive source, and the radioactive source may be provided to the applicator through a series of connecting guide tubes. The radioactive source remains in place for a specified length of time and then may be drawn back through the tubes to the afterloader machine. The applicator may be then removed from the treatment site.

Careful placement of the applicator, and thus, placement of the radioactive source is important to allow for localized and precise irradiation of the tumor. Additionally, ease of placement and positioning of the applicator is significant to improve the comfort of the patient during brachytherapy treatment.

SUMMARY

An applicator device is provided. In one example, the applicator device may include a connecting unit. The connecting unit may include a first connector coupled to a first colpostat and a second connector coupled to a second colpostat. The first connector may include a first contact portion and a body portion, the first contact portion being immovably fixed to the body portion. The second connector may include a second contact portion and a third contact portion, the second contact portion being configured to contact and pivotally engage the first contact portion. The first connector further may include a fourth contact portion configured to contact the third contact portion. The second contact portion and the third contact portion are disposed between the first contact portion and the fourth contact portion, and the first contact portion are disposed in closer proximity to a point of delivery of a radiation source than the second, third, or fourth contact portions.

Example embodiments are described in more detail below with reference to the appended figures.

BRIEF DESCRIPTION OF THE DRAWINGS

FIG. 15A illustrates a perspective view of the embodiment. FIG. 15B illustrates a side view of the embodiment of FIG. 15A. FIG. 15C illustrates a top plan view of the embodiment of FIG. 15A.

FIG. 16A illustrates a perspective view of the embodiment. FIG. 16B illustrates a side view of the embodiment of FIG. 16A. FIG. 16C illustrates a top plan view of the embodiment of FIG. 16A.

FIG. 17A illustrates a perspective view of the embodiment. FIG. 17B illustrates a side view of the embodiment of FIG. 17A. FIG. 17C illustrates a top plan view of the embodiment of FIG. 17A.

FIG. 18A illustrates a perspective view of the embodiment. FIG. 18B illustrates a side view of the embodiment of FIG. 18A. FIG. 18C illustrates a top plan view of the embodiment of FIG. 18A.

FIG. 19A shows a perspective view of the embodiment, and FIG. 19B shows a top plan view of the embodiment.

FIG. 20A shows a perspective view of the embodiment, and FIG. 20B shows a top plan view of the embodiment.

DETAILED DESCRIPTION

Figure 1:
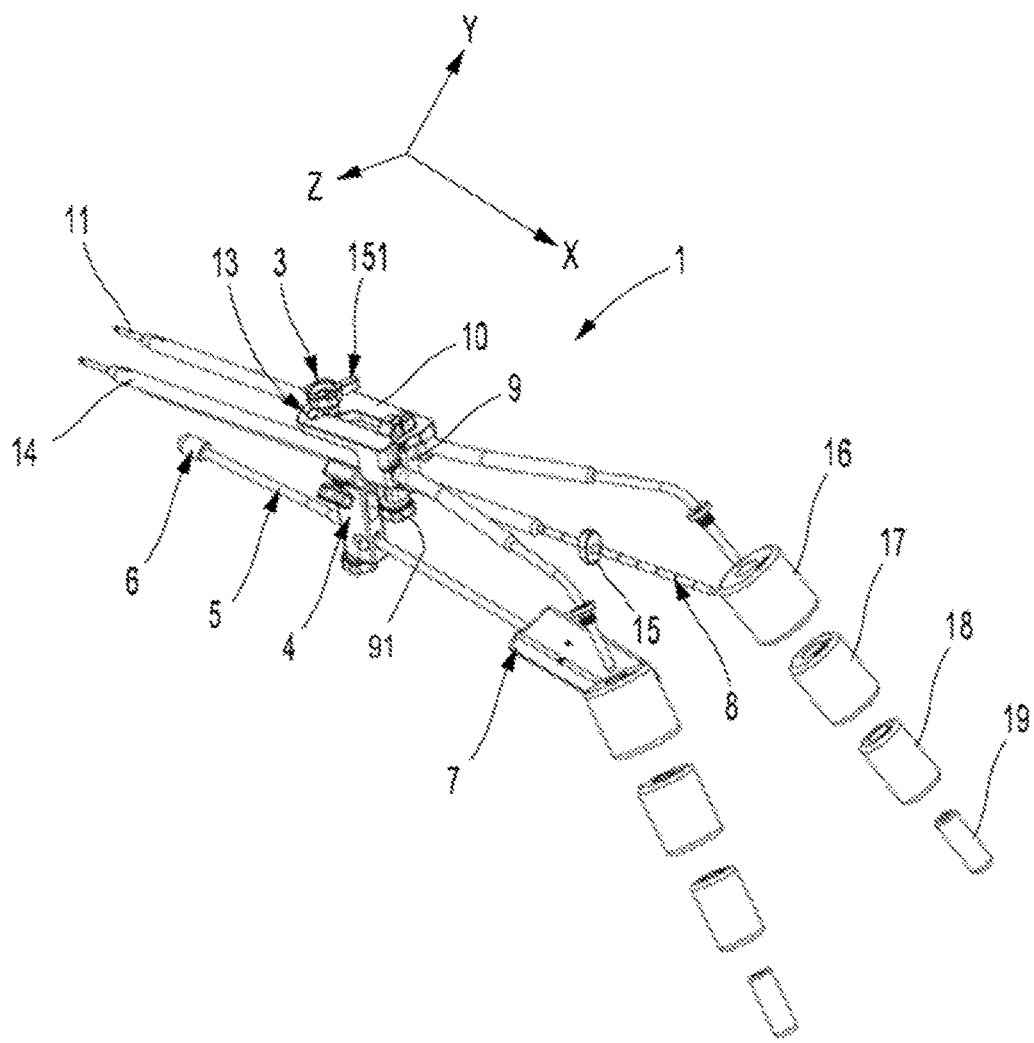
FIG. 1 illustrates a Fletcher-type brachytherapy applicator device for use in intracavity application of a radioactive source according to a first embodiment.

In the detailed description, like reference characters denote like parts in the several figures.

FIG. 1 illustrates a Fletcher-type brachytherapy applicator device 1 for use in intracavity application of a radioactive source according to a first embodiment. Applicator device 1 may comprise a connecting unit including a left colpostat spacing bracket, hereinafter referred to as a first connector 10, coupled to left colpostat 11, and a right colpostat spacing bracket, hereinafter referred to as a second connector 13, coupled to right colpostat 14. Colpostats 11 and 14, which may be spread laterally, may provide for intravaginal positioning of tandem 8, through which the radioactive source may be provided to the cervix. Spacing bracket tandem clamp 9, also shown in FIG. 14, may couple central tandem 8 to left colpostat spacing bracket 10. And cervical stop 15 may be attached toward a distal end of central tandem 8.

The applicator device may further include a rectal paddle 7 coupled to a rectal paddle bracket block 4 by a rectal paddle shaft 5. A rectal paddle end knob 6 may be fixed to a proximal end of rectal paddle shaft 5. And rectal paddle bracket block 4 may be coupled to central tandem 8.

When colpostats 11 and 14 are properly positioned, fastening unit 3 may be fastened, which may bind arm member 151 of second connector 13 to a top surface of first connector, to fix the distal ends of colpostats 11 and 14 in position along the vaginal wall.

As shown in FIG. 1, cylindrical ovoids 16, 17, 18, 19 of various sizes may be attached to the distal ends of left colpostat 11 and right colpostat 14, and the distal ends of left colpostat 11 and right colpostat 14 may be angled. In the first embodiment, central tandem 8 may be straight at the distal end. However, in other embodiments, the distal end of central tandem 8 may be curved.

Figure 2:
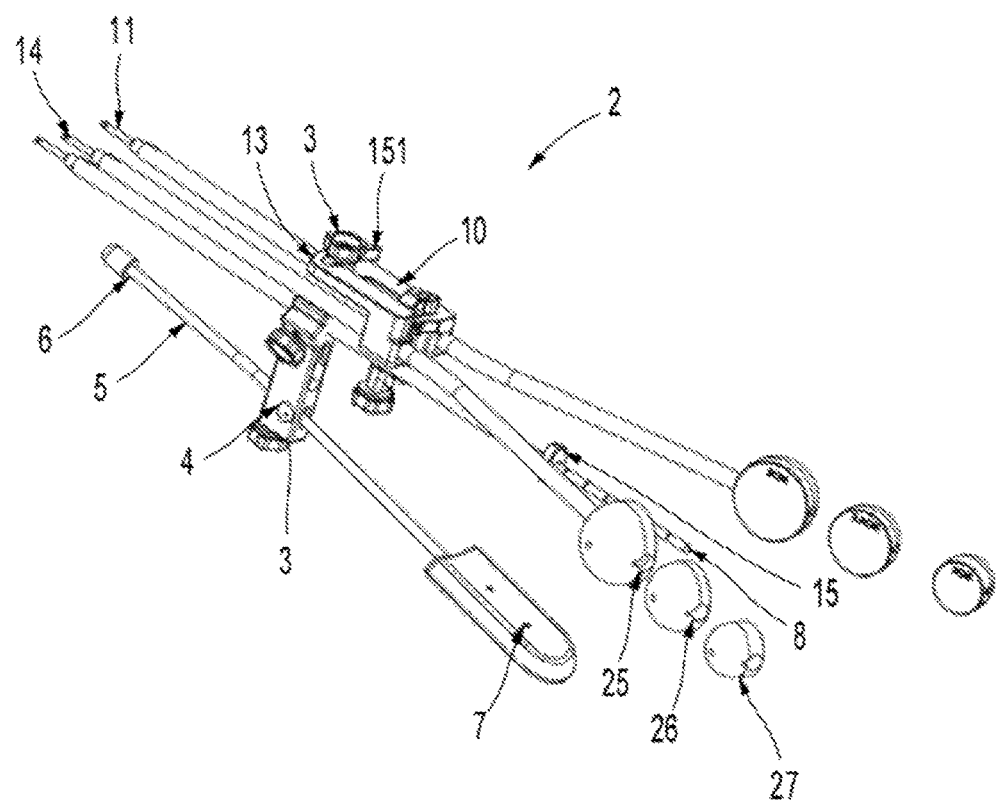
FIG. 2 illustrates a Henschke-type brachytherapy applicator device for use in intracavity application of a radioactive source according to a second embodiment.

FIG. 2 illustrates a Henschke-type brachytherapy applicator device 2 that may be used in intracavity application of a radioactive source according to another embodiment. Like reference characters of FIG. 2 show the same or similar features as FIG. 1. Applicator device 2 may include semispherical ovoids 25, 26, 27 of various size that may be attached to the distal ends of left colpostat 11 and right colpostat 14. In the second embodiment, central tandem 8 may be straight at the distal end. However, in other embodiments, the distal end of central tandem 8 may be curved.

Figure 3:
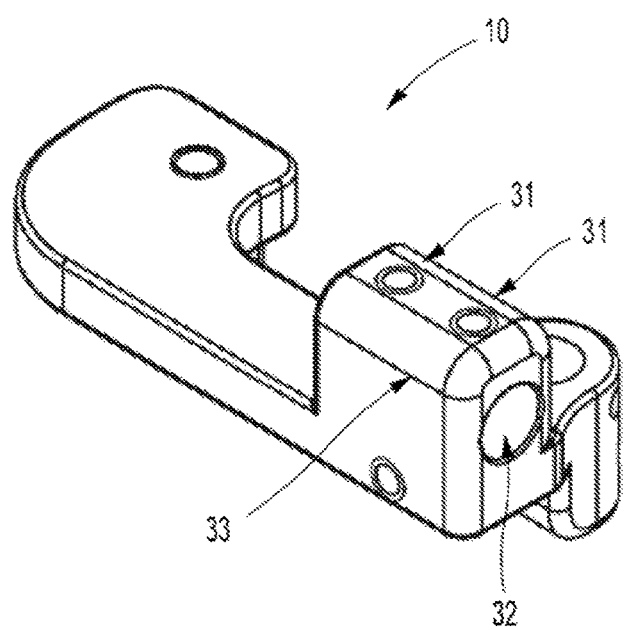
FIG. 3 illustrates a bottom perspective view of a first connector.
Figure 7:
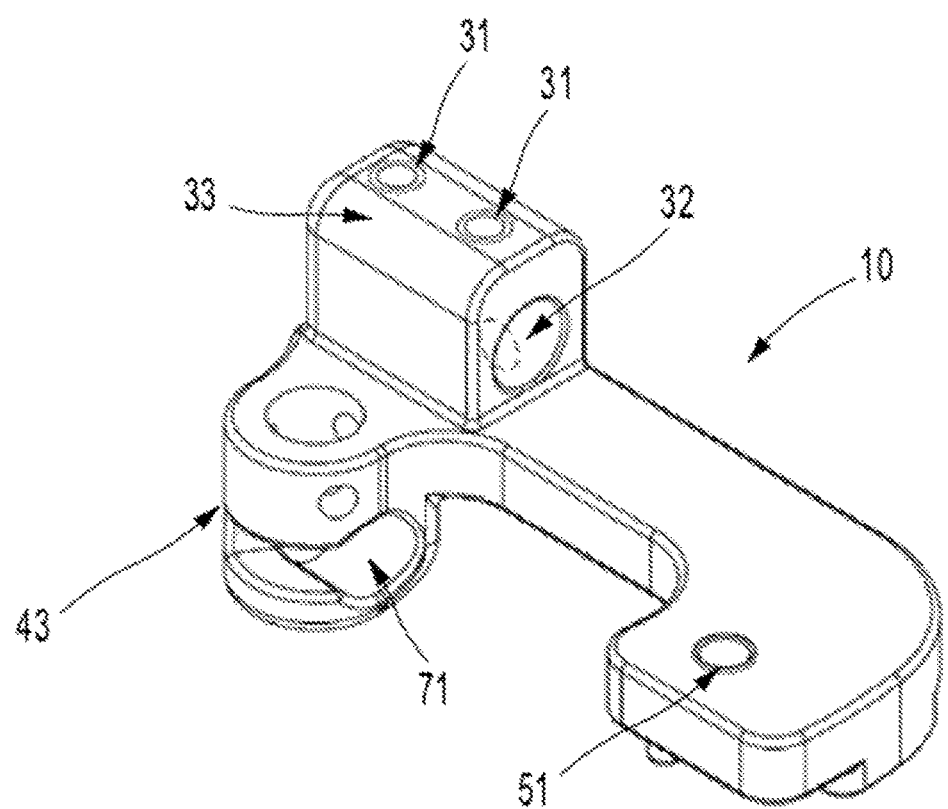
FIG. 7 illustrates a bottom perspective view of a first connector.
Figure 8:
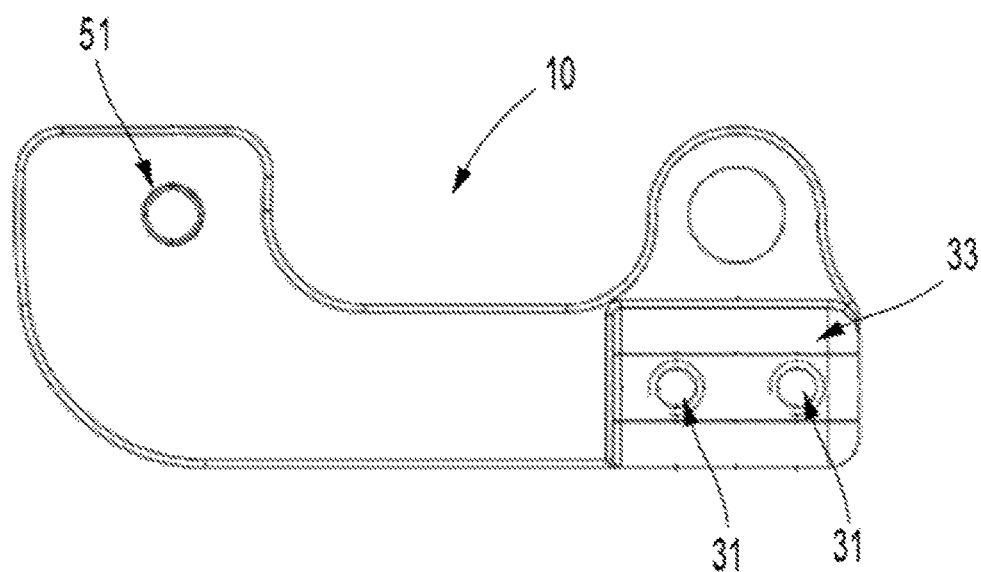
FIG. 8 illustrates a bottom plan view of first connector.

FIGS. 3 and 7 illustrate bottom perspective views of left colpostat spacing bracket or first connector 10. FIG. 8 shows a bottom plan view of first connector 10. Left colpostat 11 may be attached to connector 10 by left colpostat coupling unit 33. Left colpostat 11 may be placed in opening 32 and fasteners (not shown) may be used to fasten left colpostat 11 to left colpostat coupling unit 33 through through-holes 31.

Figure 4:
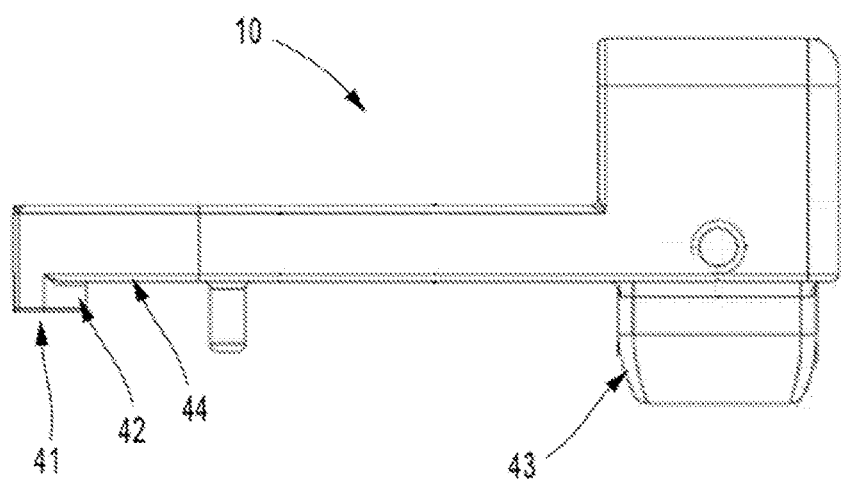
FIG. 4 illustrates a side elevation view of the first connector.
Figure 5:
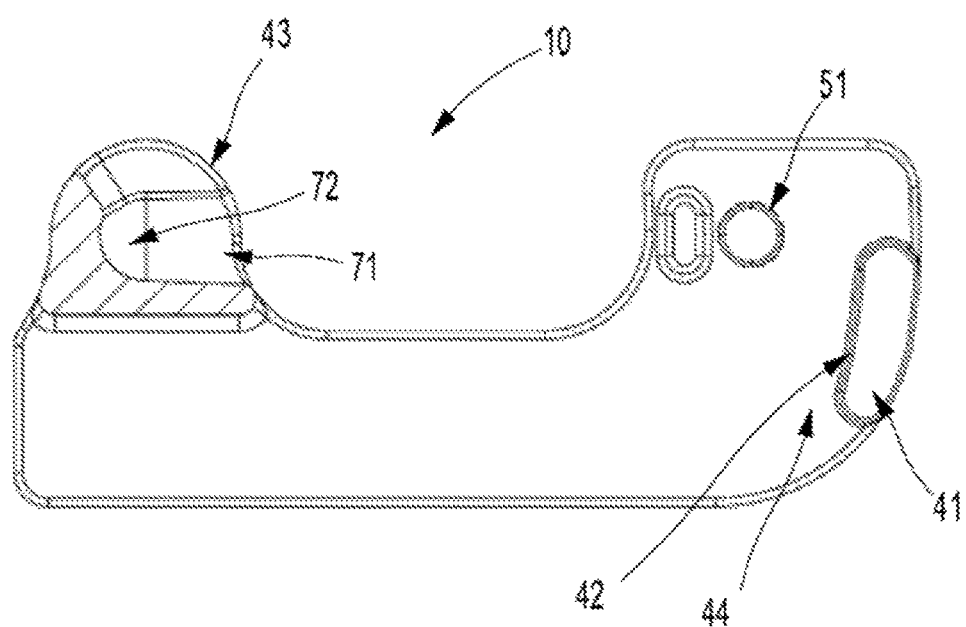
FIG. 5 illustrates a top plan view of the first connector.
Figure 6:
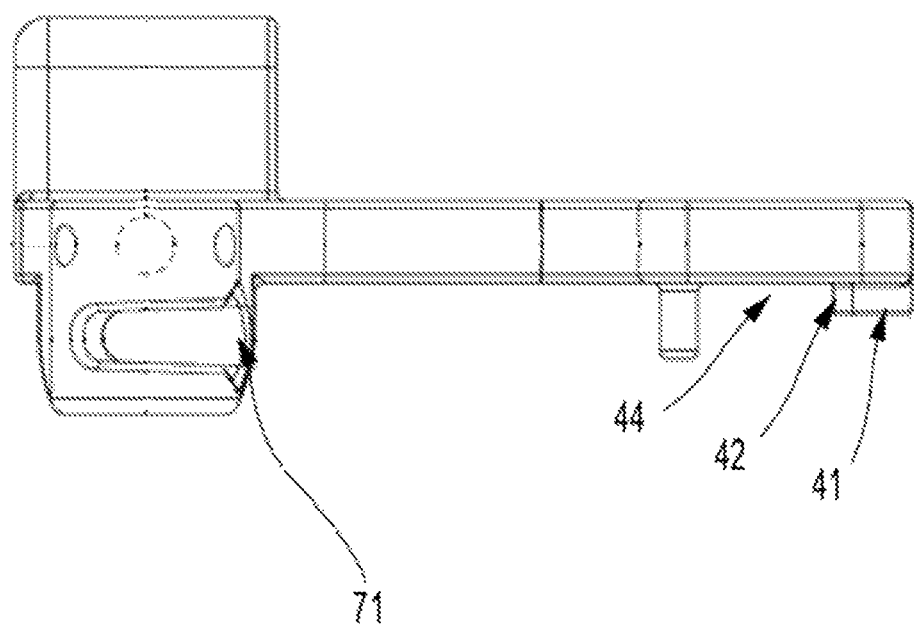
FIG. 6 illustrates a side elevation view of the first connector.

FIGS. 4 and 6 show respective side elevational views of connector 10 showing raised portion 41, which my protrude from a top surface 44 of connector 10. Raised portion 41 may have a lateral surface 42. FIGS. 5 and 6 further show concavity 71, which in this embodiment, may be a socket member including concave surface 72, configured to engage a convex member, in this embodiment, the convex member being ball member 153 protruding from second connector 13 (as shown in FIGS. 9-12). Concavity 71 may open toward the proximal end of connector 10 and toward raised portion 41, which may be positioned toward the proximal end of first connector 10.

FIG. 5 shows a top plan view of connector 10 showing raised portion 41, which may protrude from top surface 44 of connector 10. Raised portion 41 may include a lateral surface 42. FIG. 5 further shows a hole 51, which may be configured to receive a shaft 211 of fastening unit 3, as shown in FIG. 21. In this embodiment, shaft 211 and hole 51 may be respectively threaded.

Figure 9:
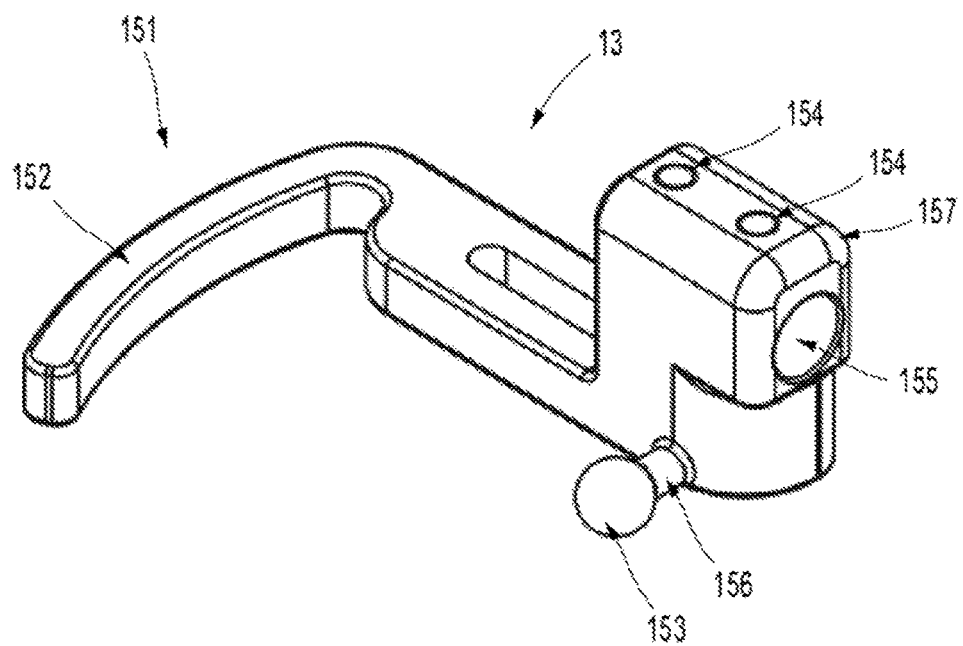
FIG. 9 illustrates a bottom perspective view of a second connector.
Figure 10:
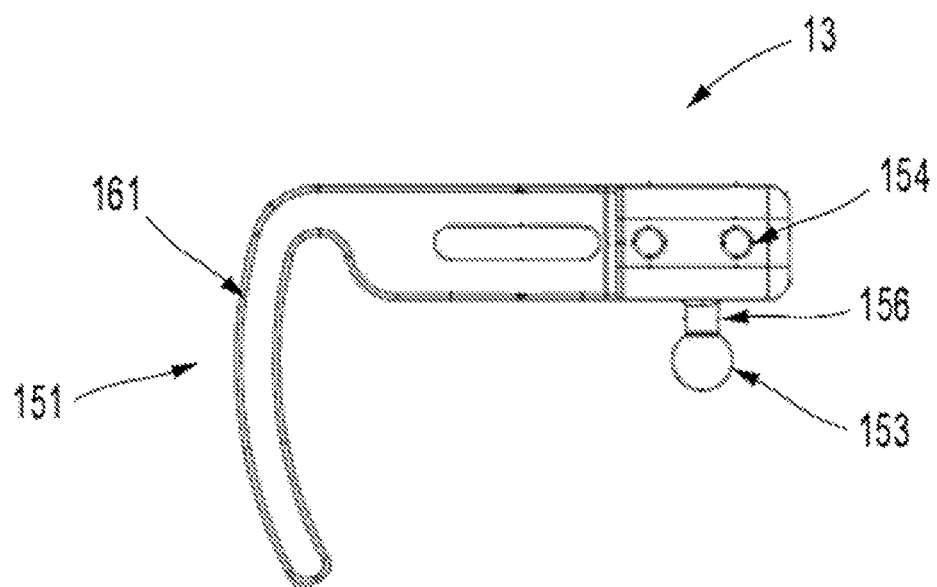
FIG. 10 illustrates a bottom plan view of the second connector.
Figure 11:
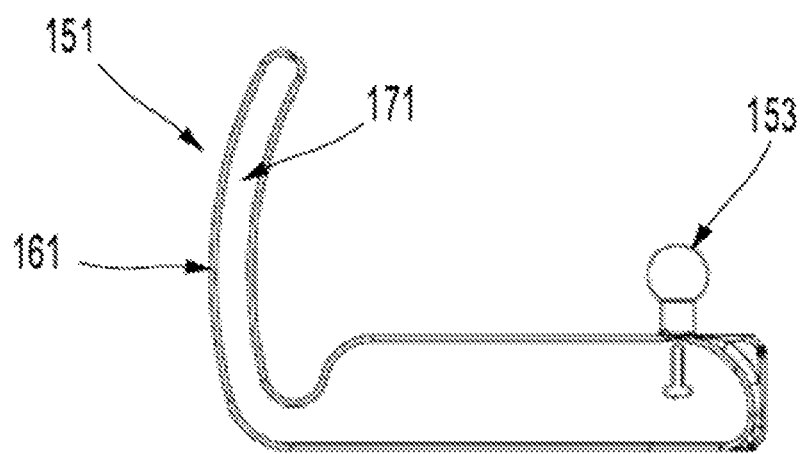
FIG. 11 illustrates a top plan view of the second connector.
Figure 12:
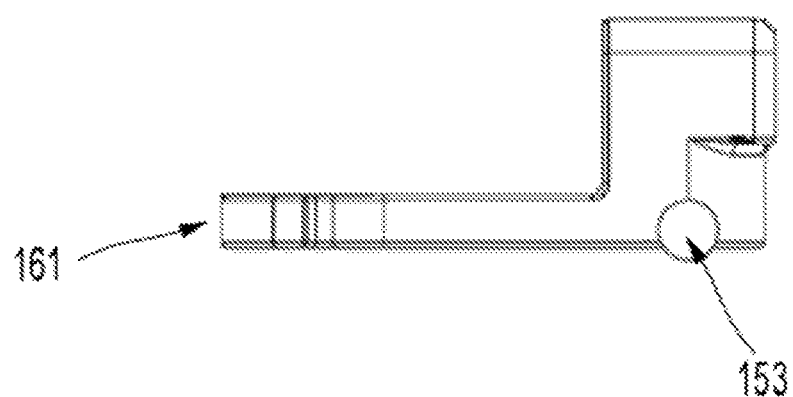
FIG. 12 illustrates a side elevation view of the second connector.
Figure 13:
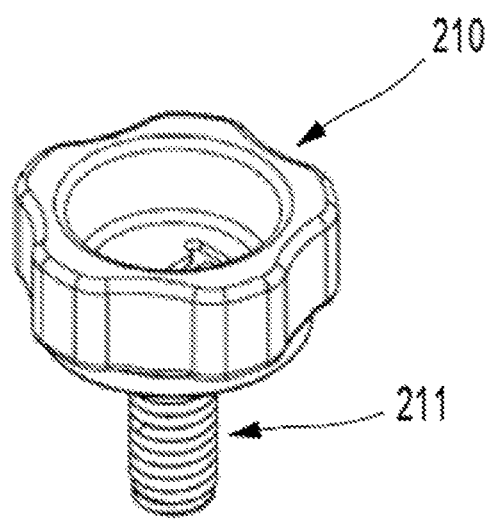
FIG. 13 illustrates a fastening unit.

FIG. 9 illustrates a bottom perspective view of right colpostat spacing bracket or second connector 13. Second connector 13 may include a protruding arm member 151 having a bottom surface 152, which may be configured to come in contact with top surface 44 of first connector 10. Additionally, as shown in FIGS. 10, 11, and 12, arm member 151 may have a proximal lateral surface 161, which may be configured to contact lateral surface 42 of raised portion 41 on the first connector 10. Fastening unit 3 may be provided to fasten second connector 13 to first connector 10 at an appropriate angle after a desired angle between left colpostat 11 and right colpostat 14 may be achieved by adjustment. As shown in FIG. 21, fastening unit 51 may include a threaded bolt having threaded shaft 211 and head 210, the underside of the head 210 (not shown) coming into contact with the top surface 171 of arm member 151, FIG. 11 showing top surface 171 of arm member 151 in a top plan view of second connector 13.

Bottom surface 152 of arm member 151 of second connector 13 may be in contact with top surface 44 of first connector 10 during adjustment and while fastened, and proximal lateral surface 161 protruding arch member 151 right colpostat spacing bracket 13 may be in contact with lateral surface 42 of raised portion 41 on left colpostat spacing bracket 10 during adjustment and while fastened, lateral surface 42 preventing travel of the right colpostat spacing bracket 13 in the proximal direction during adjustment and after being fastened.

As shown in FIG. 9, right colpostat 14 may be coupled to second connector 13 by right colpostat coupling unit 157. Right colpostat 14 may be placed in opening 155 and fasteners (not shown) may be used to fasten right colpostat 14 to right colpostat coupling unit 157 through through-holes 154.

Further, ball member 153 may be coupled to second connector 13 by stem 156. And ball member 153 may be configured to be received by concave member 43, operatively coupling first connector 10 to second connector 13, as shown in FIGS. 1 and 2.

Figure 14:
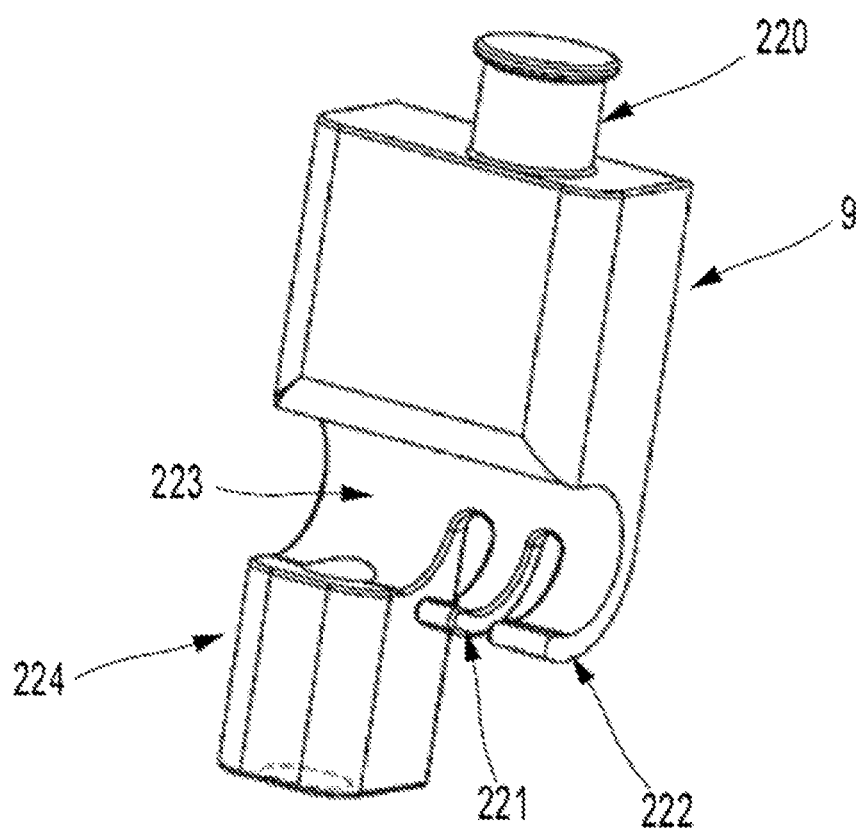
FIG. 14 illustrates a spacing bracket tandem clamp.

As shown in FIG. 14, spacing bracket tandem clamp 9 may include attachment head 220, configured to be coupled to either first connector 10 or second connector 13. Spacing bracket tandem clamp 9 may further include fingers, for example center finger 221 and outer finger 222, configured to couple within the tandem receiving portion 223. Spacing bracket tandem claim 9 may further include a fastening mechanism 224 having hole 225 through which a fastener 91 (shown, for example, in FIG. 1) may a secure and hold in position a shaft of tandem 8.

Figure 15A:
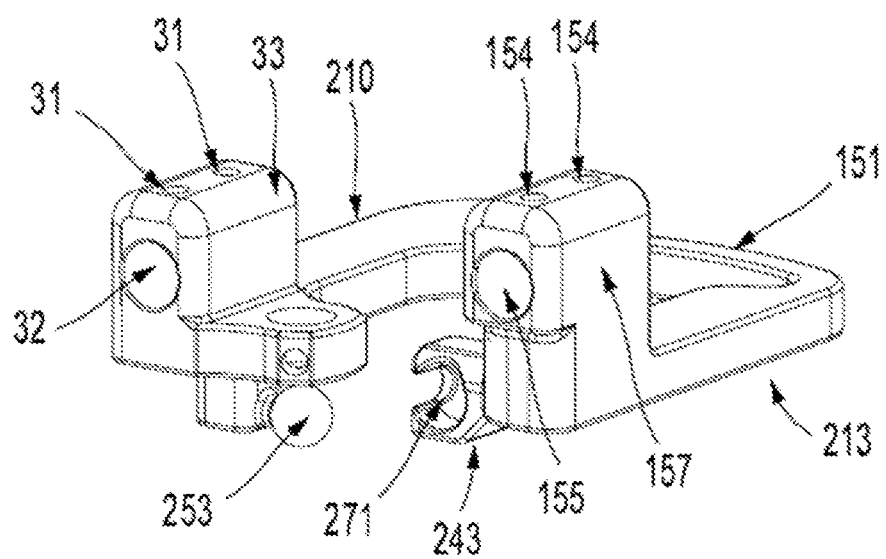
FIGS. 15A, 15B, and 15C illustrate another embodiment of the applicator device.
Figure 15B:
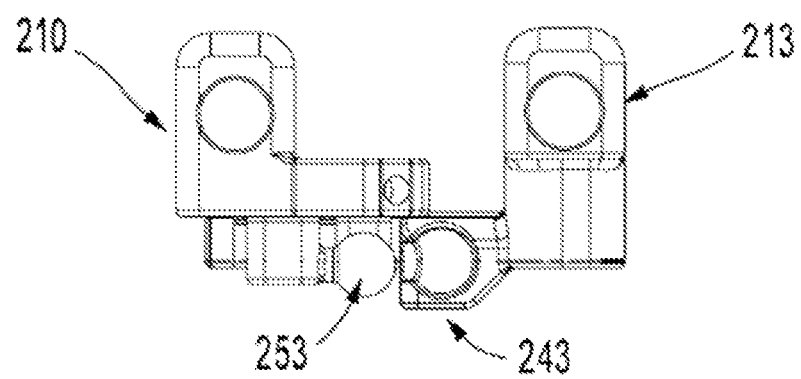
Figure 15C:
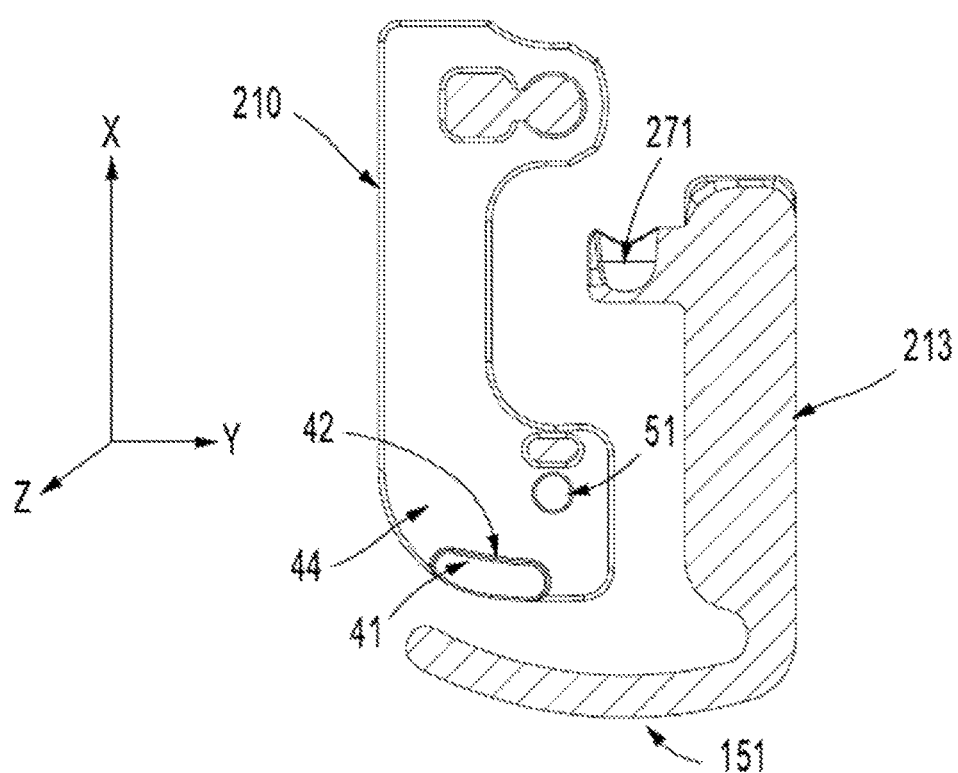

In another embodiment, as shown in FIGS. 15A, 15B, and 15C, first connector 210 may include a convex member, in this embodiment ball member 253, and second connector 213 may include concavity 243, which may include concave surface 271. In this embodiment, concavity 243 may be a socket. Like reference characters of other embodiments denote like or similar parts in FIGS. 15A, 15B, and 15C.

Figure 16A:
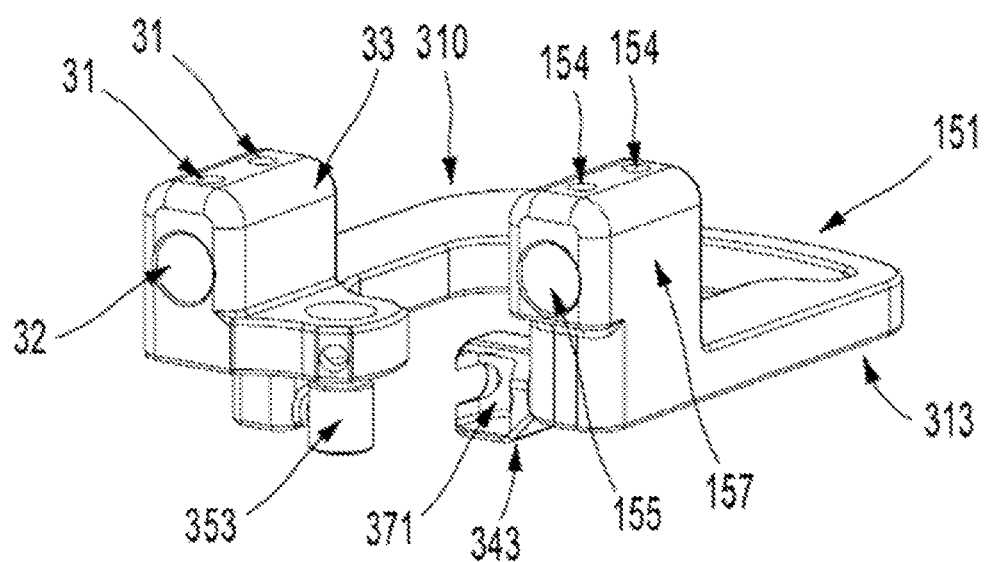
FIGS. 16A, 16B, and 16C illustrate another embodiment of the applicator device.
Figure 16B:
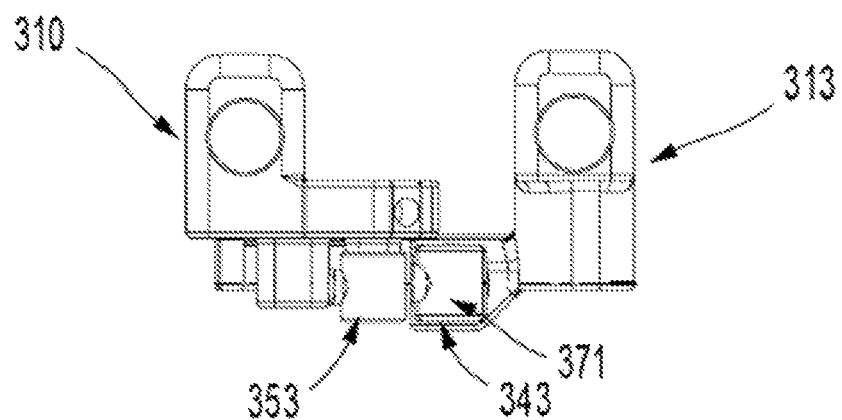
Figure 16C:
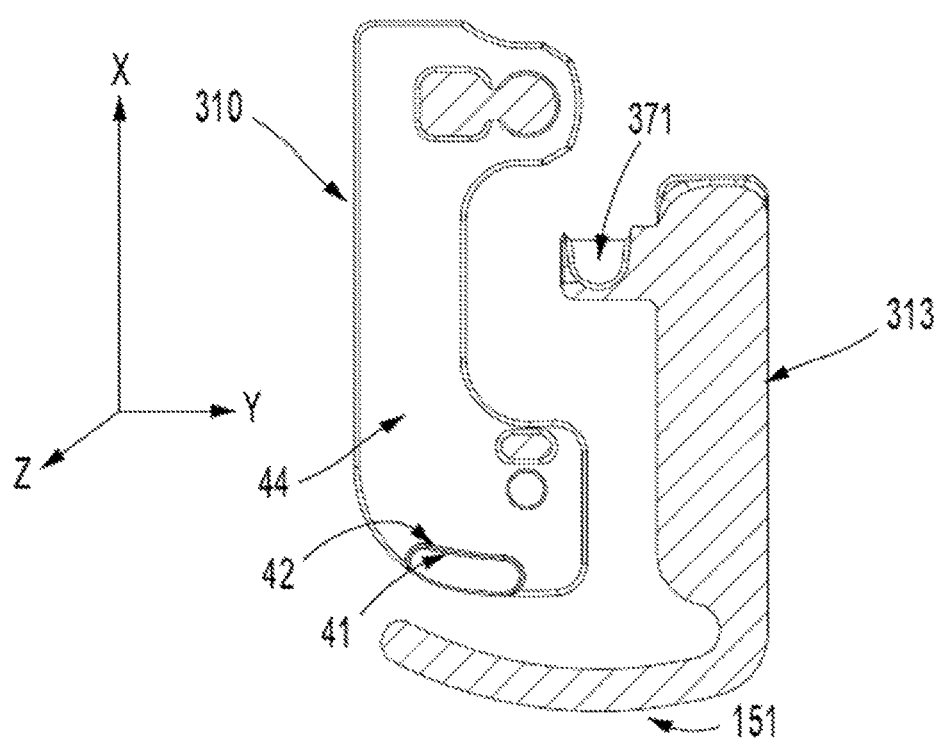

In another embodiment, as shown in FIGS. 16A, 16B, and 16C, first connector 310 may include a convex member, in this embodiment cylindrical shaft member 353, and second connector 313 may include concavity 343, which may include concave surface 371. In this embodiment, concavity 343 may be a housing member configured to engage cylindrical shaft member 353. Cylindrical shaft member 353 may be perpendicular or nearly perpendicular to the first surface 44 of first connector 310. Like reference characters of other embodiments denote like or similar parts in FIGS. 16A, 16B, and 16C.

Figure 17A:
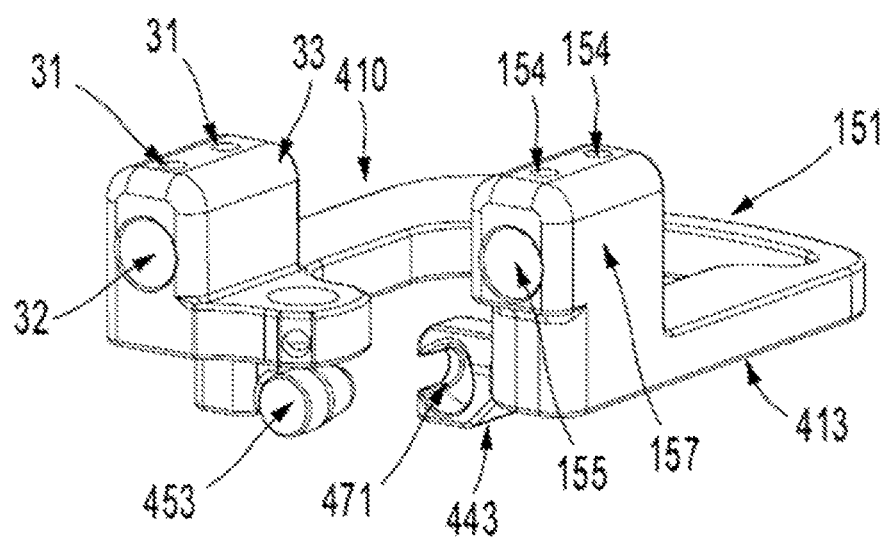
FIGS. 17A, 17B, and 17C illustrate another embodiment of the applicator device.
Figure 17B:
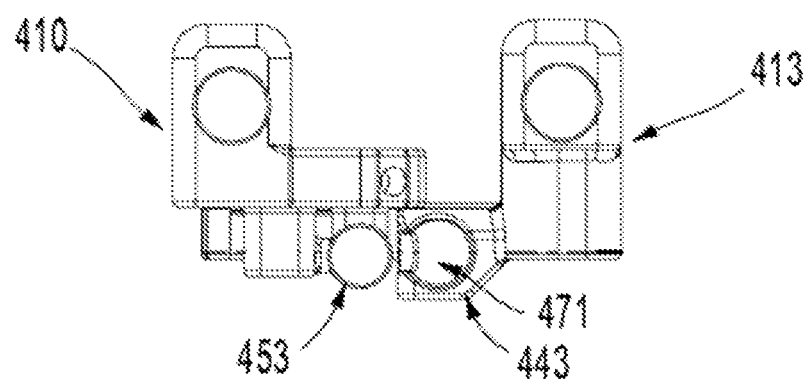
Figure 17C:
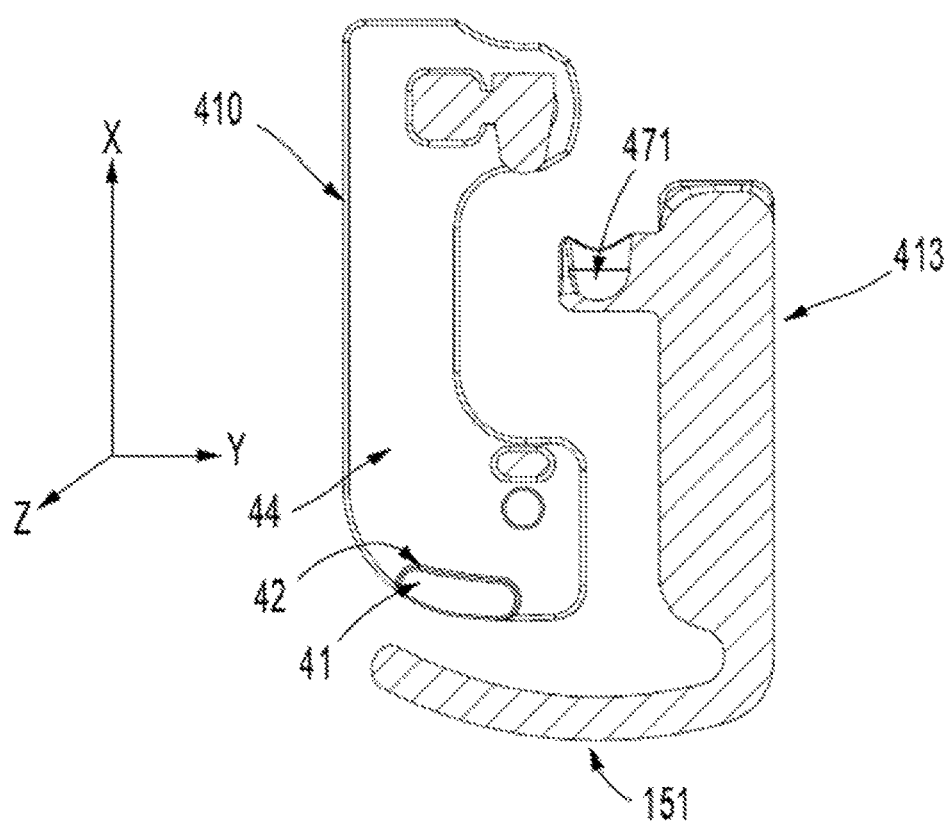

In another embodiment, as shown in FIGS. 17A, 17B, and 17C, first connector 410 may include a convex member, in this embodiment cone member 453, and second connector 413 may include concavity 443, which may include a concave surface 471. In this embodiment, concavity 443 may be a conical housing member configured to engage cone member 453. Like reference characters of other embodiments denote like or similar parts in FIGS. 17A, 17B, and 17C.

Figure 18A:
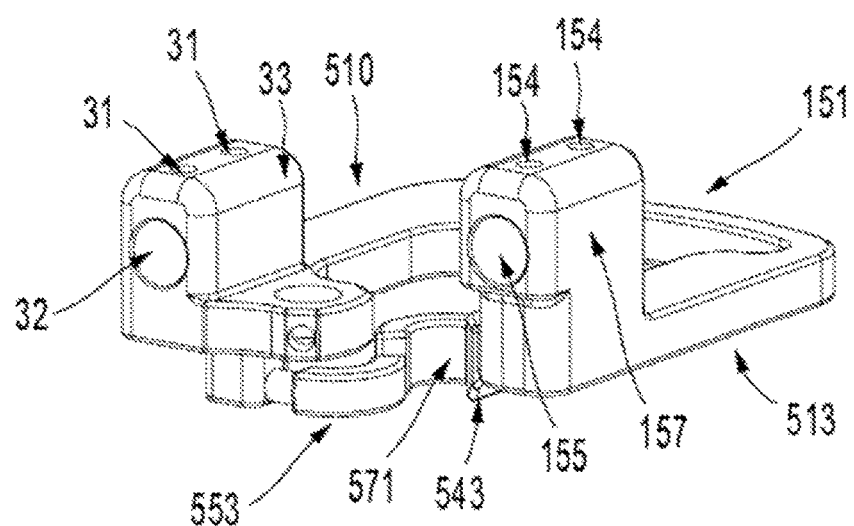
FIGS. 18A, 18B, and 18C illustrate another embodiment of the applicator device.
Figure 18B:
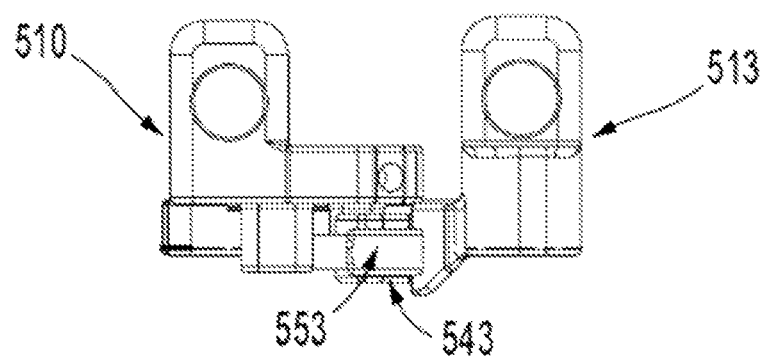
Figure 18C:
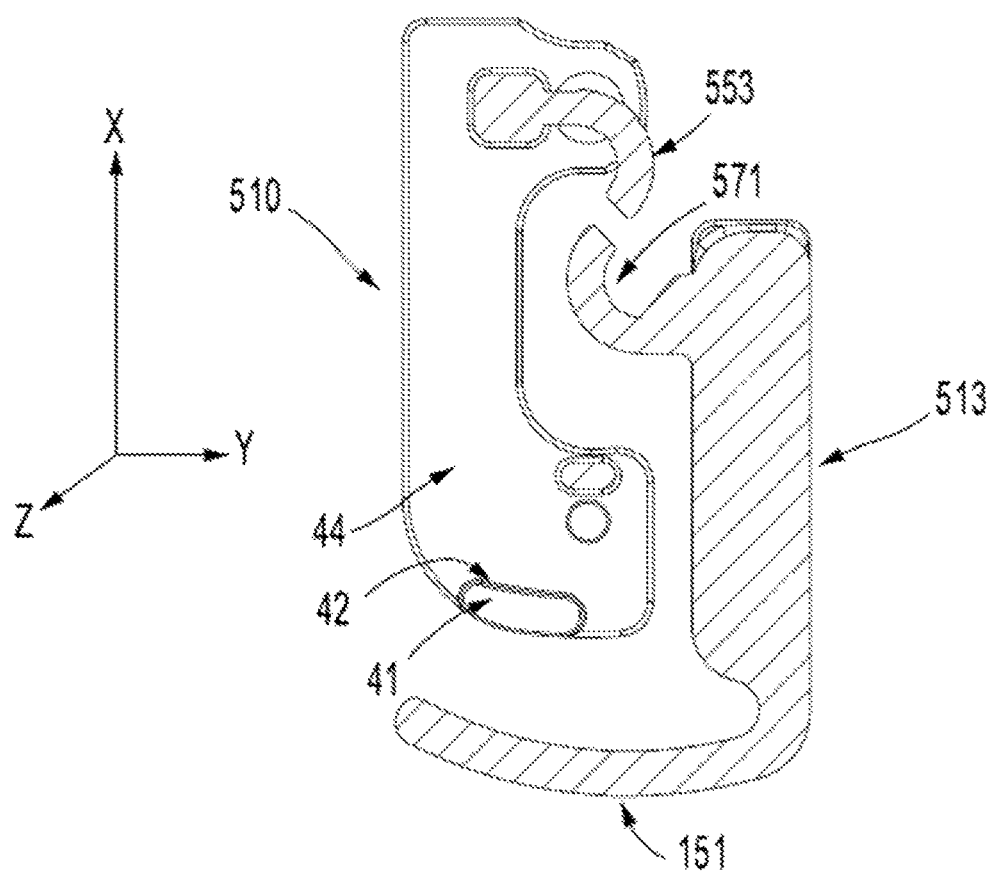

In another embodiment, as shown in FIGS. 18A, 18B, and 18C, first connector 510 may include a convex member, in this embodiment protruding hook member 553, and second connector 513 may include concavity 543, which may include concave surface 571. In this embodiment, concavity 543 may be a receiving hooking member configured to engage protruding hook member 553. Like reference characters of other embodiments denote like or similar parts in FIGS. 18A, 18B, and 18C.

Figure 19A:
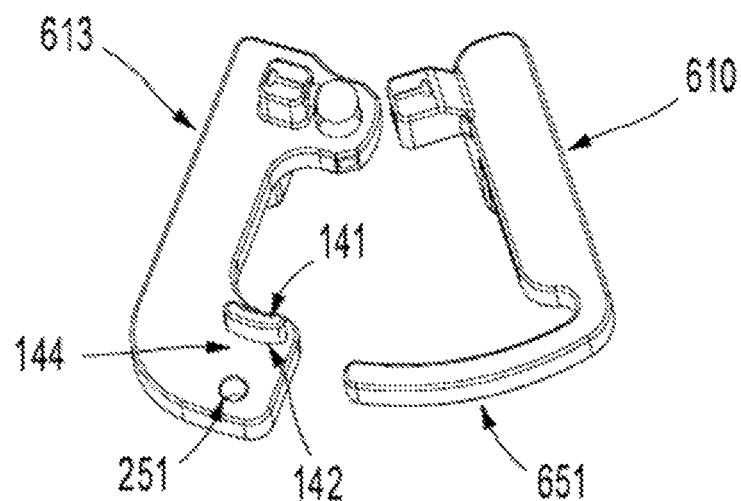
FIGS. 19A and 19B illustrate another embodiment of the applicator device.
Figure 19B:
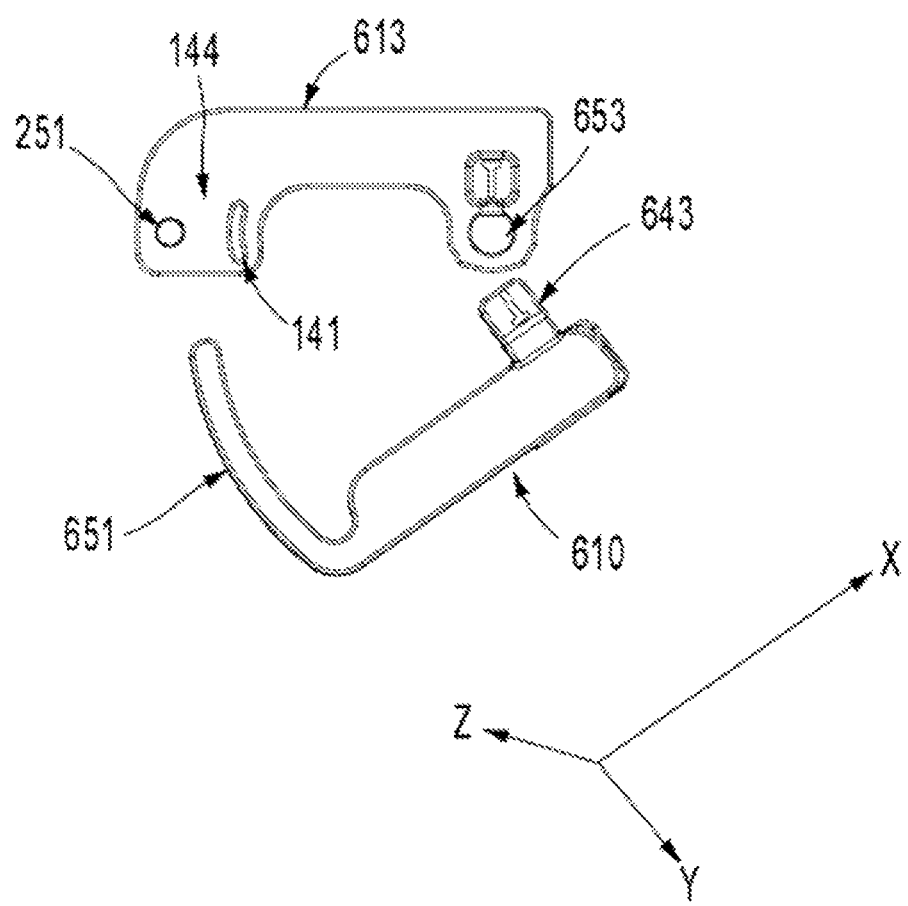

In another embodiment, as shown in FIGS. 19A and 19B, first connector 610 may include arm member 651, which may be configured to contact lateral surface 142 of raised portion 141, protruding from first surface 144 of second connector 613. Additionally, through-hole 251 may be formed toward a proximal end portion of second connector 613. Like reference characters of other embodiments denote like or similar parts in FIGS. 19A and 19B.

In another embodiment, as shown in FIGS. 19A and 19B, first connector 610 may include arm member 651, which may be configured to contact lateral surface 142 of raised portion 141, protruding from first surface 144 of second connector 613. Second connector may include convex member, for example ball member 653 protruding from a body of the second connector. Ball member 653 may be configured to be received by concave member 643, operatively coupling first connector 610 to second connector 613. Additionally, through-hole 251 may be formed toward a proximal end portion of second connector 613, through-hole 215 being configured to receive a fastening unit 210. Like reference characters of other embodiments denote like or similar parts in FIGS. 19A and 19B.

Figure 20A:
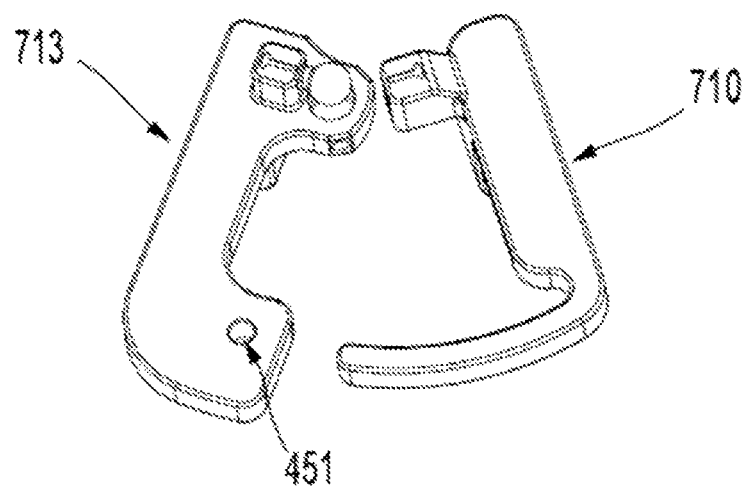
FIGS. 20A and 20B illustrate another embodiment of the applicator device.
Figure 20B:
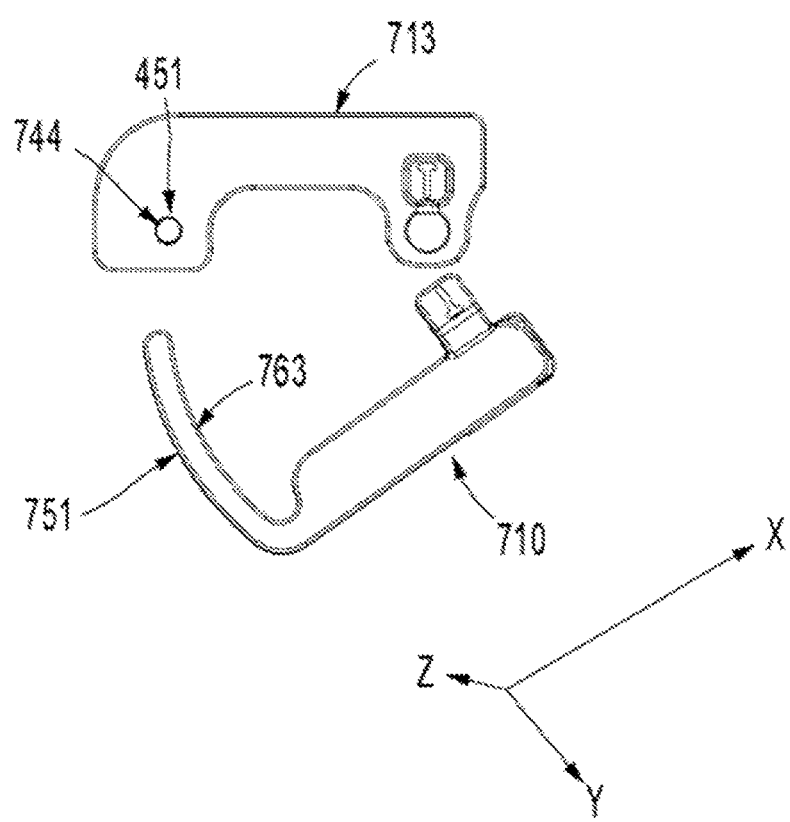

In another embodiment, as shown in FIGS. 20A and 20B, first connector 710 may include arm member 751 having a distal lateral surface 763. Distal lateral surface 763 may be perpendicular or nearly perpendicular to first surface 744 of second connector 713. Thus, arm member 751 may be configured to contact shaft 211 of fastening unit 210 (both not shown), through-hole 451 being configured to receive fastening unit 210. Contact lateral surface 142 of raised portion 141, protruding from first surface 144 of second connector 613. Additionally, through-hole 251 may be formed toward a proximal end portion of second connector 613, through-hole 215 being configured to receive a fastening unit 210. Like reference characters of other embodiments denote like or similar parts in FIGS. 19A and 19B.

In the above embodiments, the first connector may include a first contact portion and a body portion. The first contact portion may be immovably fixed to the body portion. The first contact portion may include either a concave member or a convex member. And the second connector may include a second contact portion. The second contact portion may be configured to contact and pivotally engage the first contact portion. The second contact portion may be either a concave member if the first contact portion may include a convex member or a convex member if the first contact portion may include a concave member.

The second connector further may include a third contact portion, and the first connector further may include a fourth contact portion, the fourth contact portion being configured to contact the third contact portion.

In the above embodiments, the second contact portion and the third contact portion may be disposed between the first contact portion and the fourth contact portion. The first contact portion may be disposed in closer proximity to a point of delivery of a radiation source than the second, third, or fourth contact portions.

In some embodiments, the first contact portion may include a concave member, for example, a socket, a housing member configured to engage a cylindrical shaft member, or receiving hooking member. But instead of a concave member, the first contact portion may include a convex member, for example, a ball, a cylindrical shaft member, or a protruding hooking member.

And in some embodiments, the third contact portion may include an arm member, while the fourth contact portion may include the raised portion protruding from the first surface of the first connector. However, in other embodiments, such as that shown in FIGS. 19A and 19B, the third contact portion may include a raised portion protruding from the first surface of the second connector.

Additionally, in other embodiments, the third contact portion may include an arm member and the fourth contact portion may include the shaft of the fastening unit, or, as shown in FIGS. 20A and 20B, in another embodiment, the third contact portion may include the shaft of the fastening unit and the fourth contact portion may include an arm member having a distal surface configured to contact the shaft of the fastening unit.

The arrangement of the first connector including a first contact portion and a fourth contact portion and the second connector including a second contact portion and a third contact portion, and the second contact portion and the third contact portion being disposed between the first contact portion and the fourth contact portion, allows the first connector to operably couple to the second connector in such a way as to prevent travel in the X-direction, as shown in the Cartesian coordinate of FIGS. 1, 15C, 16C, 17C, 18C, 19B, and 20B. However, while engaged, the first connector and the second connector may pivot in the Y-direction, as shown in the Cartesian coordinate of FIGS. 1, 15C, 16C, 17C, 18C, 19B, and 20B. Additionally, embodiments incorporating the ball and socket, as either the first contact portion or the second contact portion, or vice-versa, allow freedom of movement in both the Y-direction and the Z-direction, while the first colpostat and the second colpostat are being positioned along the vaginal wall. In any case, positioning and placement of the applicator may be performed with more ease, precision, and efficiency due to the first contact portion being immovably coupled to the first connector or right colpostat spacing bracket.

In addition, the present disclosure may be configured as described below.

1. An applicator device comprising:
a connecting unit including a first connector coupled to the first colpostat and a second connector coupled to the second colpostat, wherein
the first connector includes a first contact portion and a body portion, the first contact portion being immovably fixed to the body portion,
the second connector includes a second contact portion and a third contact portion, the second contact portion being configured to contact and pivotally engage the first contact portion,
the first connector further includes a fourth contact portion configured to contact the third contact portion, and
the second contact portion and the third contact portion are disposed between the first contact portion and the fourth contact portion, the first contact portion being disposed in closer proximity to a point of delivery of a radiation source than the second, third, or fourth contact portions.

2. The applicator device according to 1 above or 3 to 33 below, wherein the first contact portion pivots around the second contact portion.

3. The applicator device according to 1 or 2 above or 4 to 33 below, wherein
the second contact portion pivots around the first contact portion.

4. The applicator device according to 1 to 3 above or 5 to 33 below, wherein
the first contact portion includes a concave portion configured to engage a convex portion of
the second contact portion.

5. The applicator device according to 1 to 4 above or 6 to 33 below, wherein
the second contact portion includes a concave portion configured to engage a convex portion of the first contact portion.

6. The applicator device according to 1 to 5 above or 7 to 33 below, wherein
the first contact portion includes a socket member, and
the second contact portion includes a ball member.

7. The applicator device according to 1 to 6 above or 8 to 33 below, wherein
the second contact portion includes a socket member, and
the first contact portion includes a ball member.

8. The applicator device according to 1 to 7 above or 9 to 33 below, wherein
the first contact portion includes a cylindrical shaft member, and
the second contact portion includes a housing member configured to engage the cylindrical shaft member.

9. The applicator device according to 1 to 8 above or 10 to 33 below, wherein
the second contact portion includes a cylindrical shaft member, and
the first contact portion includes a housing member configured to pivotally engage the cylindrical shaft member.

10. The applicator device according to 1 to 9 above or 11 to 33 below, wherein
the first contact portion includes a hooking member, and
the second contact portion includes a receiving member configured to pivotally engage the hooking member.

11. The applicator device according to 1 to 10 above or 12 to 33 below, wherein
the second contact portion includes a hooking member, and
the first contact portion includes a receiving member configured to pivotally engage the hooking member.

12. The applicator device according to 1 to 11 above or 13 to 33 below, wherein
the second contact portion may be immovably fixed to a body portion of the second connector.

13. The applicator device according to 1 to 12 above or 14 to 33 below, wherein
the third contact portion includes an arm member, the arm member including a first surface configured to contact a first surface of the first connector and a second surface configured to contact the fourth contact portion.

14. The applicator device according to 1 to 13 above or 15 to 33 below, wherein
the fourth contact portion includes an arm member, the arm member including a first surface configured to contact a first surface of the second connector and a second surface configured to contact the third contact portion.

15. The applicator device according to 1 to 14 above or 16 to 33 below, wherein
the fourth contact portion includes a raised portion protruding from the first connector, the raised portion including a lateral surface configured to engage the second surface of the arm member.

16. The applicator device according to 1 to 15 above or 17 to 33 below, wherein
the third contact portion includes a raised portion protruding from the second connector, the raised portion including a lateral surface configured to engage the second surface of the arm member.

17. The applicator device according to 1 to 16 above or 18 to 33 below, further comprising
a fastening unit configured to fasten the arm member to the first connector, the fastening unit including a shaft arranged on a side of the arm member opposite from raised portion, the arm member configured to operatively pass between the shaft of the fastening unit and the lateral surface of the raised portion.

18. The applicator device according to 1 to 17 above or 19 to 33 below, further comprising
a fastening unit configured to fasten the arm member to the second connector, the fastening unit including a shaft arranged on a side of the arm member opposite from raised portion, the arm member configured to operatively pass between the shaft of the fastening unit and the lateral surface of the raised portion.

19. The applicator device according to 1 to 18 above or 20 to 33 below, wherein
the fastening unit is a threaded bolt, an underside surface of a head of the threaded bolt being configured to contact a top surface of the arm member and bind the arm member to the first surface of the first connector.

20. The applicator device according to 1 to 19 above or 21 to 33 below, wherein
the fastening unit is a threaded bolt, an underside surface of a head of the threaded bolt being configured to contact a top surface of the arm member and bind the arm member to the first surface of the second connector.

21. The applicator device according to 1 to 20 above or 22 to 33 below, wherein
the fourth contact portion includes a fastening unit configured to fasten the arm member to
the first connector, the fastening unit including a shaft configured to contact the second surface of the arm member.

22. The applicator device according to 1 to 21 above or 23 to 33 below, wherein
the third contact portion includes a fastening unit configured to fasten the arm member to the second connector, the fastening unit including a shaft configured to contact the second surface of the arm member.

23. The applicator device according to 1 to 22 above or 24 to 33 below, wherein
the fastening unit is a threaded bolt, an underside surface of a head of the threaded bolt being configured to contact a top surface of the arm member and bind the arm member to the first surface of the first connector.

24. The applicator device according to 1 to 23 above or 25 to 33 below, wherein
the fastening unit is a threaded bolt, an underside surface of a head of the threaded bolt being configured to contact a top surface of the arm member and bind the arm member to the first surface of the second connector.

25. The applicator device according to 1 to 24 above or 26 to 33 below, wherein the first surface of the arm member is nearly perpendicular to the second surface of the arm member, and
the first surface of the arm member is nearly parallel to the first surface of the first connector.

26. The applicator device according to 1 to 25 above or 27 to 33 below, wherein
the first surface of the arm member is nearly perpendicular to the second surface of the arm member, and
the first surface of the arm member is nearly parallel to the first surface of the second connector.

27. The applicator device according to 1 to 26 above or 28 to 33 below, further comprising
a tandem coupled to the connecting unit.

28. The applicator device according to 1 to 27 above or 29 to 33 below, wherein
the tandem is coupled to the first connector or the second connector.

29. The applicator device according to 1 to 28 above or 30 to 33 below, wherein
a distal end of the first colpostat and a distal end of the second colpostat are configured to be spread laterally by movement operation of the first connector or the second connector.

30. The applicator device according to 1 to 29 above or 31 to 33 below, further comprising
a first ovoid coupled to a distal end of the first colpostat, and
a second ovoid coupled to a distal end of the second colpostat.

31. The applicator device according to 1 to 30 above or 32 or 33 below, wherein
the first ovoid and the second ovoid are each cylindrical or semi-cylindrical.

32. The applicator device according to 1 to 31 above or 33 below, wherein
the first ovoid and the second ovoid are each spherical or semi-spherical.

33. The applicator device according to 1 to 32 above or 5 to 33 below, further comprising
a paddle support unit coupled to the connecting unit, the paddle support unit including a paddle coupled to a paddle shaft.

34. A brachytherapy method for treating cancer, the method comprising:
inserting an applicator device according to 1 to 33 above into, the applicator device including a first connector coupled to the first colpostat and a second connector coupled to the second colpostat, the first connector including a first contact portion and a body portion, the first contact portion being immovably fixed to the body portion, the second connector including a second contact portion and a third contact portion, the second contact portion being configured to contact and pivotally engage the first contact portion, the first connector further including a fourth contact portion configured to contact the third contact portion, and the second contact portion and the third contact portion being disposed between the first contact portion and the fourth contact portion, the first contact portion being disposed in closer proximity to a point of delivery of a radiation source than the second, third, or fourth contact portions;
adjusting a lateral spacing between distal ends of the first colpostat and the second colpostat; and
applying a radioactive treatment to a cervix from the radiation source provided within the applicator device.

While various embodiments of the present invention have been described above, and although various examples and experiments disclosing various aspects of the present invention have been disclosed, it should be understood that they have been presented by way of example only, and not limitation. It will be understood by those skilled in the art that various changes in form and details may be made therein without departing from the spirit and scope of the invention as defined in the appended claims. Accordingly, the breadth and scope of the present invention should not be limited by any of the above-described exemplary embodiments, but should be defined only in accordance with the following claims and their equivalents.

The invention claimed is:
1. An applicator device comprising:
a connecting unit including a first connector coupled to a first colpostat and a second connector coupled to a second colpostat, wherein
the first connector includes a first contact portion and a body portion, the first contact portion being immovably fixed to the body portion,
the second connector includes a second contact portion and a third contact portion, the second contact portion being configured to contact and pivotally engage the first contact portion,
the first connector further includes a fourth contact portion configured to contact the third contact portion, and
the second contact portion and the third contact portion are disposed between the first contact portion and the fourth contact portion, the first contact portion being disposed in closer proximity to a point of delivery of a radiation source than the second, third, or fourth contact portions,
wherein
the third contact portion includes a raised portion that protrudes from a body portion of the second connector and the raised portion is immovably fixed in relation to the body portion of the second connector, and the fourth contact portion includes an arm member configured to contact a surface of the raised portion,
or
the fourth contact portion includes a raised portion that protrudes from the body portion of the first connector and the raised portion is immovably fixed in relation to the body portion of the first connector, and the third contact portion includes an arm member configured to contact a surface of the raised portion.

2. The applicator device according to claim 1, wherein
the first contact portion pivots around the second contact portion, or
the second contact portion pivots around the first contact portion.

3. The applicator device according to claim 2, wherein
in the case that the first contact portion pivots around the second contact portion, the first contact portion includes a concave portion configured to engage a convex portion of the second contact portion, or
in the case that the second contact portion pivots around the first contact portion, the second contact portion includes a concave portion configured to engage a convex portion of the first contact portion.

4. The applicator device according to claim 3, wherein
in the case that the first contact portion pivots around the second contact portion, the first contact portion includes a socket member and the second contact portion includes a ball member, or
in the case that the second contact portion pivots around the first contact portion, the second contact portion includes a socket member and the first contact portion includes a ball member.

5. The applicator device according to claim 4, wherein the ball member includes a spherical ball portion.

6. The applicator device according to claim 3, wherein
in the case that the first contact portion pivots around the second contact portion, the first contact portion includes a cylindrical shaft member and the second contact portion includes a housing member configured to pivotally engage the cylindrical shaft member, or
in the case that the second contact portion pivots around the first contact portion, the second contact portion includes a cylindrical shaft member and the first contact portion includes a housing member configured to pivotally engage the cylindrical shaft member.

7. The applicator device according to claim 3, wherein
in the case that the first contact portion pivots around the second contact portion, the first contact portion includes a hooking member and the second contact portion includes a receiving member configured to pivotally engage the hooking member, or
in the case that the second contact portion pivots around the first contact portion, the second contact portion includes a hooking member and the first contact portion includes a receiving member configured to pivotally engage the hooking member.

8. The applicator device according to claim 1, wherein the second contact portion is immovably fixed to a body portion of the second connector.

9. The applicator device according to claim 1, wherein
in the case that the third contact portion includes an arm member, the arm member includes a first surface configured to contact a first surface of the first connector and a second surface configured to contact the fourth contact portion, or
in the case that the fourth contact portion includes an arm member, the arm member includes a first surface configured to contact a first surface of the second connector and a second surface configured to contact the third contact portion.

10. The applicator device according to claim 9, wherein
in the case that the third contact portion includes an arm member, the fourth contact portion includes the raised portion protruding from the first connector, the raised portion including a lateral surface configured to engage the second surface of the arm member, or
in the case that the fourth contact portion includes an arm member, the third contact portion includes the raised portion protruding from the second connector, the raised portion including a lateral surface configured to engage the second surface of the arm member.

11. The applicator device according to claim 10, wherein
in the case that the third contact portion includes an arm member, the applicator device further comprises a fastening unit configured to fasten the arm member to the first connector, the fastening unit including a shaft arranged on a side of the arm member opposite from raised portion, the arm member configured to operatively pass between the shaft of the fastening unit and the lateral surface of the raised portion, or
in the case that the fourth contact portion includes an arm member, the applicator device further comprises a fastening unit configured to fasten the arm member to the second connector, the fastening unit including a shaft arranged on a side of the arm member opposite from the raised portion, the arm member configured to operatively pass between the shaft of the fastening unit and the lateral surface of the raised portion.

12. The applicator device according to claim 11, wherein
in the case that the third contact portion includes an arm member, the fastening unit is a threaded bolt, an underside surface of a head of the threaded bolt being configured to contact a top surface of the arm member and bind the arm member to the first surface of the first connector, or
in the case that the fourth contact portion includes an arm member, the fastening unit is a threaded bolt, an underside surface of a head of the threaded bolt being configured to contact a top surface of the arm member and bind the arm member to the first surface of the second connector.

13. The applicator device according to claim 9, wherein
in the case that the third contact portion includes an arm member, the fourth contact portion includes a fastening unit configured to fasten the arm member to the first connector, the fastening unit including a shaft configured to contact the second surface of the arm member, or
in the case that the fourth contact portion includes an arm member, the third contact portion includes a fastening unit configured to fasten the arm member to the second connector, the fastening unit including a shaft configured to contact the second surface of the arm member.

14. The applicator device according to claim 13, wherein
in the case that the third contact portion includes an arm member, the fastening unit is a threaded bolt, an underside surface of a head of the threaded bolt being configured to contact a top surface of the arm member and bind the arm member to the first surface of the first connector, or
in the case that the fourth contact portion includes an arm member, the fastening unit is a threaded bolt, an underside surface of a head of the threaded bolt being configured to contact a top surface of the arm member and bind the arm member to the first surface of the second connector.

15. The applicator device according to claim 9, wherein
in the case that the third contact portion includes an arm member, the first surface of the arm member is nearly perpendicular to the second surface of the arm member and the first surface of the arm member is nearly parallel to the first surface of the first connector, or
in the case that the fourth contact portion includes an arm member, the first surface of the arm member is nearly perpendicular to the second surface of the arm member and the first surface of the arm member is nearly parallel to the first surface of the second connector.

16. The applicator device according to claim 1, wherein at least a part of the first contact portion is disposed in closer proximity to a point of delivery of a radiation source than the second, third, and fourth contact portions are disposed to the point of delivery of the radiation source.

17. The applicator device according to claim 16, wherein a tandem is coupled to the first connector or the second connector.

18. The applicator device according to claim 1, wherein a distal end of the first colpostat and a distal end of the second colpostat are configured to be spread laterally by movement operation of the first connector or the second connector.

19. The applicator device according to claim 1, further comprising
a first ovoid coupled to a distal end of the first colpostat, and a second ovoid coupled to a distal end of the second colpostat.

20. The applicator device according to claim 1, wherein, in the case that the third contact portion includes the raised portion that protrudes from the body portion of the second connector and the raised portion is immovably fixed to the body portion of the second connector, the raised portion includes a smooth lateral surface configured to engage a surface of the fourth contact portion, or in the case that the fourth contact portion includes the raised portion that protrudes from the body portion of the first connector and the raised portion is immovably fixed to the body portion of the first connector, the raised portion includes a smooth lateral surface configured to engage a surface of the third contact portion.

21. The applicator device according to claim 1, wherein, in the case that the third contact portion includes the raised portion that protrudes from the body portion of the second connector and the raised portion is immovably fixed to the body portion of the second connector, the raised portion includes a lateral surface configured to engage a surface of the fourth contact portion, the lateral surface having a convex surface portion with a convexity directed toward the fourth contact portion, or in the case that the fourth contact portion includes the raised portion that protrudes from the body portion of the first connector and the raised portion is immovably fixed to the body portion of the first connector, the raised portion includes a lateral surface configured to engage a surface of the third contact portion, the lateral surface having a concave surface portion with a concavity opening toward the third contact portion.

22. The applicator device according to claim 1, wherein, in the case that the third contact portion includes the a raised portion that protrudes from the body portion of the second connector and the raised portion is immovably fixed to the body portion of the second connector, the raised portion has a base diameter at a base of the raised portion and a top-most diameter at a top-most free distal end of the raised portion, and the top-most diameter is less than or equal to the base diameter, or in the case that the fourth contact portion includes the raised portion that protrudes from the body portion of the first connector and the raised portion is immovably fixed to the body portion of the first connector, the raised portion has a base diameter at a base of the raised portion and a top-most diameter at a top-most free distal end of the raised portion, and the top-most diameter is less than or equal to the base diameter.

23. A brachytherapy method for treating cancer, the method comprising:

inserting an applicator device, the step of inserting the applicator device including inserting a first colpostat and inserting a second colpostat, the first colpostat being coupled to a first connector and the second colpostat being coupled to a second connector, the first connector including a first contact portion and a body portion, the first contact portion being immovably fixed to the body portion, the second connector including a second contact portion and a third contact portion, the second contact portion being configured to contact and pivotally engage the first contact portion, the first connector further including a fourth contact portion configured to contact the third contact portion, and the second contact portion and the third contact portion being disposed between the first contact portion and the fourth contact portion, the first contact portion being disposed in closer proximity to a point of delivery of a radiation source than the second, third, or fourth contact portions, wherein the third contact portion includes a raised portion that protrudes from a body portion of the second connector and the raised portion is immovably fixed in relation to the body portion of the second connector, and the fourth contact portion includes an arm member configured to contact a surface of the raised portion, or the fourth contact portion includes a raised portion that protrudes from the body portion of the first connector and the raised portion is immovably fixed in relation to the body portion of the first connector, and the third contact portion includes an arm member configured to contact a surface of the raised portion;

adjusting a lateral spacing between distal ends of the first colpostat and the second colpostat; and applying a radioactive treatment from the radiation source provided within the applicator device.

\* \* \* \* \*